United States Patent [19]

Mitchell

[11] Patent Number: 4,795,833
[45] Date of Patent: Jan. 3, 1989

[54] PROCESS FOR PREPARING A MIXTURE OF METHYL-SUBSTITUTED PRIMARY ANILINES

[75] Inventor: Richard S. Mitchell, Newark, Del.

[73] Assignee: E. I. Du Pont de Nemours and Company, Wilmington, Del.

[21] Appl. No.: 10,843

[22] Filed: Feb. 4, 1987

[51] Int. Cl.$^4$ .............................................. C07C 85/24
[52] U.S. Cl. ..................................... 564/409; 564/305
[58] Field of Search ................................ 564/409, 305

[56] References Cited

U.S. PATENT DOCUMENTS

| | | | |
|---|---|---|---|
| 3,868,420 | 2/1975 | Evans et al. | 260/578 |
| 3,931,298 | 1/1976 | Wollensak | 260/581 |
| 3,960,962 | 6/1976 | Shubkin | 260/581 |
| 4,188,341 | 2/1980 | Fischer | 260/573 |
| 4,317,931 | 3/1982 | Wollensak et al. | 564/409 |
| 4,480,128 | 10/1984 | Arpe et al. | 564/424 |
| 4,554,380 | 11/1985 | Arpe et al. | 564/424 |
| 4,593,113 | 6/1986 | Weigert | 564/409 |

FOREIGN PATENT DOCUMENTS

| | | |
|---|---|---|
| 29178 | 8/1974 | Japan . |
| 53-28128 | 3/1978 | Japan . |
| 53-28129 | 3/1978 | Japan . |

OTHER PUBLICATIONS

Matsumoto, Chemistry Letters, pp. 939-942 (1977).
Inoue, et al., Sekiyu Gakkaishi, 15:372 (1972).
Matsumoto, et al., Chemistry Letters, pp. 435-438 (1978).

Primary Examiner—Glennon H. Hollrah
Assistant Examiner—John A. Sopp

[57] ABSTRACT

A process is disclosed for preparing an isomeric mixture of methyl-substituted aniline comprising contacting at least one of said analines with a specified zeolite catalyst.

16 Claims, No Drawings

PROCESS FOR PREPARING A MIXTURE OF METHYL-SUBSTITUTED PRIMARY ANILINES

BACKGROUND OF THE INVENTION

FIELD OF THE INVENTION

This invention concerns a process for preparing isomeric mixtures of methyl-substituted anilines.

BACKGROUND OF THE INVENTION

Methyl-substituted anilines are useful in a variety of applications such as in the preparation of dyes, herbicides, plant growth agents and antiknock agents for gasoline engines. The anilines are generally prepared by nitration of the appropriate methyl benzene followed by reduction of the resulting nitro compound. This process depends upon the availability of the appropriate nitro compound which in some instances is unavailable or available only in limited quantities. For example, the 3,5-dimethylaniline is important as an intermediate. However, in the foregoing nitration-reduction process, nitration of m-xylene gives predominantly 2,4-dimethylaniline, i.e., 86%. Only 14% of the dimethylanilines produced is 2,6-dimethylaniline and 0% is 3,5-dimethylanilines.

U.S. Pat. No. 3,868,420 discloses a process for producing phenylamines alkylated in the ortho and/or para positions by alkyl groups of 1–4 carbon atoms and unsubstituted on the amino group which comprises reacting a suitable phenylamine with an alkanol of 1–4 carbon atoms in the vapor phase at a temperature of from 350° C. to 450° C. in the presence of an aluminum oxide catalyst or an aluminum oxide/molybdenum oxide mixed catalyst.

U.S. Pat. No. 3,931,298 discloses a process for converting hydroxy-substituted aromatic compounds to the corresponding amine by reacting the aromatic hydroxy compound with ammonia in the presence of a catalytic amount of a cyclohexane and in contact with a hydrogen-transfer catalyst, most preferably palladium. U.S. Pat. No. 3,960,962 discloses a similar process wherein the catalyst comprises metallic palladium bonded to a phosphinated polystyrene resin.

U.S. Pat. No. 4,188,341 discloses a process for making 2,6-dimethylaniline or an N-substituted 2,6-dimethylaniline comprising reacting an enamine of a specified formula at a temperature of between −30° C. and 150° C. with acrolein in the presence of an inert aprotic solvent and heating the resulting reaction product to a temperature of between 100° C. and 400° C. in the presence of a hydrogen-transfer catalyst and an amine of the formula $RNH_2$ wherein R is −H or a specified lower alkyl.

U.S. Pat. No. 4,480,128 and the apparent equivalent European Patent Application No. 92,103 disclose a process for preparing o-toluidine and/or m-toluidine and/or p-toluidine in two steps: (a) treatment of a toluidine isomer mixture or any undesired toluidine isomer with an isomerization catalyst from the series of the synthetic zeolites of the pentasil type, (b) isolation of the desired or one of the desired isomers from the mixture of isomers formed in step (a) through selective adsorption on a medium or large pore zeolite and subsequent desorption.

U.S. Pat. No. 4,593,124 discloses a process for preparing an isomeric mixture of a monomethyl-, dimethyl- or monoethyl-substituted aniline consisting essentially of contacting at least one of said anilines with a specified zeolite at about 250° C.–500° C. and about 10 kPa to 10 MPa, said zeolite catalyst having pores with dimensions of from about 0.5 nm to less than about 0.7 nm and having cages with dimensions no greater than about 0.7 nm, with the proviso that the dimethyl-substituted anilines can only be 2,4-, 2,5- and 3,4-dimethylanilines.

Japanese Patent Application Publication Kokai No. 53-28128 discloses a process for para-methylation of anilines comprising reacting an aniline having para-hydrogens with methanol in the presence of an alkali metal synthetic zeolite catalyst, particularly NaY zeolite. Preparation of 2,4-dimethylaniline from o-toluidine and the preparation of p-toluidine from aniline are specifically disclosed.

T. Matsumoto, *Chemistry Letters*, p. 939 (1977), discloses the ortho-methylation of 2,3-dimethylaniline with methanol over various solid catalysts with 5 wt % Ag on $Al_2O_3$ showing the highest selectivity to orthomethylation, that is, the production of 2,3,6-trimethylaniline. aniline.

M. Inoue et al., *Sekiyu Gakkaishi*, 15:372 (1972) studied the methylation of aromatic compounds with methanol in vapor or liquid phase on various catalysts and specifically report the ortho-methylation of aniline with methanol using 10% $MgO/Al_2O_3$ catalyst to produce o-toluidine.

Japanese Patent Publication No. 28129/1978 discloses demethylation of polymethylanilines, which contain at least more than two methyl groups, in the presence of a catalyst composition of the formula $A_aB_bC_cO_d$ wherein A is titanium; B represents more than one kind of element selected from zinc, zirconium and magnesium; C represents more than one kind of element, selected from vanadium, chromium, manganese, tin, iron, cobalt, nickel, copper, molybdenum, tungsten, barium, calcium; O is oxygen, a is 1, b is 0.05 to about 20, and c is 0 to 1.0. Reaction temperatures of 440°–600° C. are disclosed. Ti-Zr catalyst systems are said to give mainly p-demethylated products, such as 2,6-xylidine from mesidine. Ti-Zn or Mg catalyst systems give o- and/or p-demethylated products, such as m-toluidine from 2,3-, 3,4-, and 2,5-dimethylaniline, 2,4,5-trimethylaniline; and 2,3,4,6-tetramethylaniline.

Japanese Patent Publication No. 1974-[Showa-49], 29,178 discloses a process for the synthesis of toluidines rich in m-toluidine by dealkylation of xylidines having a methyl group in a meta position at 400°–700° C. in the presence of a dealkylation catalyst such as silica-alumina, alumina, silica, silica-magnesia and magnesia.

Matsumoto et al., Chemistry Letters, pp 435–438 (1978) disclose a process for preparing m-toluidine by hydrocracking 2,3-xylidine over metal oxide-supported nickel catalysts. The authors disclose that the selectivity of m-toluidine is influenced by side reactions, such as isomerization, and that the extent of isomerization can be related to the acidic character of the metal oxide carriers.

SUMMARY OF THE INVENTION

The present invention provides a process for preparing an isomeric mixture of methyl-substituted aniline having the formula

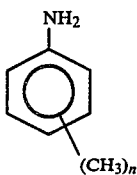

wherein n is 2 or 3, said process comprising contacting at least one compound of formula I with an acidic zeolite catalyst at a temperature of from about 240° C. to about 550° C. and at a pressure of from about 10 kPa to about 10 MPa, said zeolite catalyst being selected from the group consisting of zeolites omega, beta, L and mixtures thereof.

DETAILED DESCRIPTION OF THE INVENTION

The present invention provides a process for preparing an isomeric mixture of methyl-substituted anilines employing an acidic zeolite catalyst selected from the group consisting of zeolites omega, beta, L and mixtures thereof. The process comprises contacting at least one compound of formula (I) with the zeolite catalyst at a temperature of from about 240° C. to about 550° C. and at a pressure of from about 10 kPa to about 10 MPa. The isomerization process of this invention can be represented by the reaction

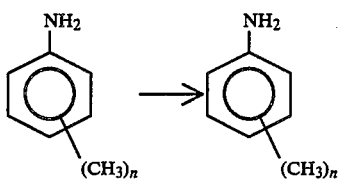

where n is 2 or 3 and the reaction product is a mixture containing isomers different from the reactant.

In the process of this invention the total number of methyl groups on the primary aniline is substantially conserved. Minor portions of the reactant may undergo reactions in which some of the methyl groups are lost. The amount of demethylation increases with increasing temperature. However, under the conditions of this process, the major portion of the reactant undergoes the reaction indicated above and the loss of methyl groups is generally less than about 5%.

Zeolites can be generically described as complex aluminosilicates characterized by a three-dimensional framework structure enclosing cavities occupied by ions and water molecules, all of which can move with significant freedom within the zeolite matrix. In commercially useful zeolites, the water molecules can be removed from or replaced within the framework without destroying its geometry. Zeolites can be represented by the following formula:

$$M_{2/n}O\ Al_2O_3 x SiO_2 y H_2O$$

wherein M is a cation of valence n, $x \geq 2$, and y is a number determined by the porosity and the hydration state of the zeolite, generally from 2 to 8. In naturally-occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

Zeolite structure consists of corner-linked tetrahedra with Al or Si atoms at centers of tetrahedra and oxygen atoms at corners. Such tetrahedra are combined in a well-defined repeating structure comprising various combinations of 4-, 5-, 6-, 8-, 10-, and 12-membered rings. The resulting framework consists of regular channels and cages, which impart a useful pore structure for catalysis. Pore dimensions are determined by the geometry of the aluminosilicate tetrahedra forming the zeolite channels or cages, with nominal openings of 0.26 nm for 6-rings, 0.40 nm for 8-rings, and 0.55 nm for 10 rings. Pore dimensions are critical to catalytic performance, since this characteristic determines whether reactant molecules can enter and product molecules can exit the zeolite framework. In practice, it has been observed that very slight decreases in ring dimensions can effectively hinder or block movement of particular reactants or products within a zeolite structure.

The pore dimensions which control access to the interior of the zeolite are determined not only by the tetrahedra forming the pore opening, but also by the presence or absence of ions in or near the pore. In the case of zeolite A, for example, access can be restricted by monovalent ions, such as $Na^+$ or $K^+$, which are situated in or near 8-ring openings as well as 6-ring openings. Access is enhanced by divalent ions, such as $Ca^{2+}$, which are situated only in or near 6-rings. Thus KA and NaA exhibit effective pore openings of about 0.3 nm and 0.4 nm respectively, whereas CaA has an effective pore opening of 0.5 nm.

Useful references generally relating to zeolite structure and characterization include the following:

Meier et al., *Atlas of Zeolite Structure Types (International Zeolite Assn.* 1978);

Mumpton, "Natural Zeolites" in *Reviews in Mineralogy* 14:1 (1977);

Smith, "Origin and Structure of Zeolites" in *Zeolite Chemistry and Catalysis,* ACS Monograph 171 (American Chemical Society, 1976).

Zeolite catalysts suitable for use in the process of the invention are selected from the group consisting of zeolites omega, beta, L and mixtures thereof. Zeolite omega is a synthetic zeolite having a composition expressed in terms of moles of oxides as $$0.5-1.5 M_{2/n}O.Al_2O_3.5-20SiO_2.0-10H_2O$$

wherein M is as described above. The cations represented by M include metal cations such as alkali metals, particularly sodium, alkaline earth metals, transition metals and rare earths as well as non-metallic cations such as hydrogen, ammonium and organic cations of the alkylonium type, particularly alkylammonium cations such as tetramethylammonium ions. The synthesis of this synthetic zeolite is described in U.S. Pat. No. 4,241,036, issued to Flanigen et al., and in Araya et al., *Zeolites,* 4:263 (1984), the disclosures of which are incorporated herein by reference. The zeolite omega can be prepared from a reaction gel containing sodium hydroxide and sources of tetramethylammonium (TMA) ions, silica, and alumina. The zeolite omega as crystallized contains both TMA and sodium cations and is the TMA, Na-form of zeolite omega. If this zeolite omega is calcined, the TMA ions decompose and the resulting zeolite omega contains no organic cations. Framework neutrality is maintained by a combination of hydrogen ions and dehydroxylated species. This zeolite can be subjected to an Na ion exchange to produce zeolite Na-omega. The synthesized zeolite TMA, Na-omega can be subjected to an ammonium ion exchange to produce zeolite NH$_4$-omega which can then be calcined to produce zeolite H-omega. Other forms of zeolite omega can be produced by ion exchange.

The crystal structure of zeolite omega is characterized by a one-dimensional system of nearly cylindrical channels running parallel to the c-axis of the zeolite. The channels are bounded by 12-membered rings of Si-AlO$_4$ tetrahedra and have a pore or aperture dimension of 0.74 nm. There is also another channel system, formed by distorted 8-member rings, which is considerably smaller in dimension and is not accessible to the main channel system.

Subsequent to the synthesis of zeolite omega, the natural zeolite mazzite was discovered. Structure studies indicate that zeolites omega and mazzite are isostructural and zeolite omega is sometimes referred to as synthetic mazzite and mazzite is sometimes referred to as zeolite omega. In addition, recent work has concluded that the TMA form of the synthetic zeolite ZSM-4 is essentially the same material as zeolite Omega. For the purposes of this invention, "zeolite omega" is intended to include the corresponding zeolites mazzite and ZSM-4, as well as other isostructural zeolites.

Zeolite beta is a synthetic zeolite having a composition expressed in terms of moles of oxides as

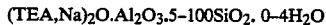
(TEA,Na)$_2$O.Al$_2$O$_3$.5–100SiO$_2$. 0–4H$_2$O where TEA represents the tetraethylammonium ion. The synthesis of this synthetic zeolite is described in U.S. Pat. No. 3,308,069, the disclosure of which is incorporated herein by reference. The zeolite beta can be prepared by crystallization from an aqueous reaction mixture containing amorphous silica solids or sols, a soluble aluminate and a source of TEA such as tetraethylammonium hydroxide. Upon heating the resulting product above 400° F., the TEA ion decomposes and zeolite H-beta is produced. Other forms of zeolite beta can be produced by ion exchange.

Zeolite L is a synthetic zeolite having a composition expressed in terms of moles of oxides as

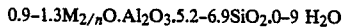
0.9–1.3M$_{2/n}$O.Al$_2$O$_3$.5.2–6.9SiO$_2$.0–9 H$_2$O wherein M is as a Group I, II, or III metal ion and other cations such as hydrogen and ammonium ions.

The synthesis of this synthetic zeolite is described in D. W. Breck, *Zeolite Molecular Sieves,* John Wiley & Sons, New York, 1974 and in U.S. Pat. No. 3,216,789, the disclosures of which are incorporated herein by reference. The zeolite L can be prepared from a sodium, potassium aluminosilicate reaction gel. Preferably, the zeolite L incorporates K and as crystallized contains mostly potassium cations. Other forms of zeolite L can be produced by ion exchange.

The crystal structure of zeolite L is characterized by a one-dimensional system of nearly cylindrical channels running parallel to the c-axis of the zeolite. The channels are bounded by 12-membered rings and have a pore or aperture dimension of 0.71 nm.

Although not wishing to be bound by theory, zeolites omega, beta and L are believed to catalyze both 1,2-intramolecular shifts and intermolecular transalkylations of methylanilines. For example, these zeolites convert any dimethylaniline (DMA) into a mixture of all six DMA's as the result of 1,2 intramolecular methyl shifts, plus some toluidines and trimethylanilines as the result of intermolecular transalkylations. The resulting product may also contain trace amounts of aniline, tetramethylaniline, and pentamethylaniline. Zeolites omega, beta and L also convert any trimethylaniline (TMA) into a mixture of all six TMA's plus some DMA's and tetramethylanilines and trace amounts of aniline, toluidines and pentamethylaniline. The amount of product methylamines which contain other than the number of methyl groups contained by the reactant methylaniline increases as the severity of the process conditions increase, e.g., as the reaction temperature and/or reaction time increases.

Regardless of which methylaniline or combination of methylanilines are fed as reactants, contact with the zeolites omega, beta and L eventually results in an equilibrium mixture containing all the methylanilines from aniline to pentamethylaniline. This statement does not apply to a feed consisting of only pentamethylaniline since there are no open positions on the benzene ring to allow for 1,2-shifts or transalkylations. The composition of the equilibrium mixture is dependent on the methyl/ring ratio of the original feed. For example, feeding a tetramethylaniline as the reactant would result in a mixture of methylanilines that contained largely penta-, tetra-, and trimethylanilines with smaller amounts of the DMA's, the toluidines and aniline.

In the process of the invention at least one compound of formula I is contacted with an acidic zeolite catalyst selected from the group consisting of omega, beta, L and mixtures thereof. Preferably, the zeolite catalyst is the hydrogen or aluminum form, i.e., zeolite H-omega, H-beta, H-L, Al-omega, Al-beta or Al-L. A temperature of from about 240° C. to about 550° C., preferably from about 280° C. to about 425° C., is employed. The process is conducted at a pressure of from about 10 kPa to about 10 MPa, preferably from about 100 kPa to about 1 MPa. Preferred reaction times are from about 0.1 second to about 10 hours. The process of the invention can be carried out in liquid or gas phase and can be conducted in batch or continuous mode. If a methylaniline reactant is a solid, a solvent may be used to feed it to the reactor system. Convenient solvents are benzene, aniline, toluene, xylene and other related solvents.

The invention is further described by the following Examples, wherein all parts and percentages are by weight and degrees are Celcius unless otherwise stated.

EXAMPLES 1–6

Isomerization of Dimethylaniline

Isomerization of dimethylaniline (DMA) when contacted with zeolite H-omega was demonstrated by passing a liquid feed comprised of a DMA feed at a rate of 3 mL/h along with nitrogen carrier gas fed at the rate of 10 mL/min at atmospheric pressure over zeolite H-omega in a 5 inch (13 cm) long, ⅜ inch (1 cm) diameter Vycor ® reactor heated with a split-tube furnace. Feed compositions and reaction temperatures are shown in Table I. The zeolite H-omega catalyst employed is commercially available from Union Carbide as ELZ-omega-6. 3.2 g of the catalyst were employed in Example 1, 10.0 g in Example 5 and 3.0 g in Examples 2, 3, 4 and 6.

In Examples 1, 2, 3 and 5, reaction products were analyzed as follows. After the process had operated for about 30 minutes, the liquid product was collected for the next 5 minutes and analyzed by gas chromatography using a 30 meter capillary column packed with a polyethylene oxide commercially available from Union Carbide under the registered trademark Carbowax ® 20M.

Elution was carried out by beginning at 100°, increasing the temperature 6° per minute until the temperature reached 200°, and then holding the temperature at 200° for one minute. The retention times increased in the order aniline, o-, p-, m-toluidine, 2,6-, 2,4-, 2,5-DMA, 2,4,6-TMA, 3,5-, 2,3-, 3,4-DMA, 2,3,6-, 2,4,5-, 2,3,5-, 3,4,5-, 2,3,4-TMA, the three tetramethylanilines and finally pentamethylaniline. The two TMA's, 3,4,5-TMA and 2,3,4-TMA, are tentatively assigned and may be interchanged in order of retention. The product compositions are shown in Table I.

In Examples 4 and 6, the reaction products were analyzed on-line by gas chromatography, i.e., instead of the liquid product being collected and then analyzed, a heated transfer line from the exit end of the reactor to the gas chromatography column was used to analyze the gas product stream directly. The product compositions are shown in Table I.

by volume of 2,5-DMA in benzene and 1 g of acidic zeolite Mg-omega as catalyst. The catalyst was prepared from a zeolite omega commercially available from Union Carbide as ELZ-omega-5. The commercially obtained zeolite omega is described as being prepared by calcining the synthesized zeolite of the TMA,-Na-form of zeolite omega and is said to contain no organic cations. The commercial zeolite omega was refluxed at 100° for two hours with a solution made by placing about a 3-fold molar excess of magnesium nitrate in water to effect a cation exchange. The resulting solution was then filtered and the zeolite so obtained was calcined at about 550° for about 16 hours. The zeolite was then refluxed for two hours in the magnesium nitrate solution described above, filtered, and calcined at about 550° for about 16 hours to yield the catalyst. The reaction temperature, product composition and Me/Ring are shown in Table II.

TABLE I

| Ex. No. | Feed | React. Temp. (°) | Product Composition (mole %) | | | | Individual DMA's | | | | | |
|---|---|---|---|---|---|---|---|---|---|---|---|---|
| | | | Anil | Tols | DMA's | 246 TMA | 23 | 24 | 25 | 26 | 34 | 35 |
| 1 | 25-DMA | 315 | 0.6 | 49.5 | 49.7 | 0.1 | 1.5 | 6.3 | 37.5 | 2.9 | 0.8 | 0.8 |
| | + | 355 | 1.8 | 49.4 | 48.4 | 0.3 | 4.3 | 10.0 | 25.2 | 5.2 | 1.8 | 2.0 |
| | m-tol | 370 | 2.2 | 51.0 | 46.5 | 0.4 | 3.9 | 9.0 | 25.2 | 4.4 | 1.9 | 1.8 |
| | (1:1 molar) | 430 | 2.0 | 49.4 | 48.4 | 0.3 | 2.6 | 8.2 | 26.1 | 4.0 | 2.4 | 2.1 |
| 2 | 24-DMA | 265 | 0.1 | 1.6 | 97.9 | 0.4 | 1.5 | 93.2 | 2.9 | 0.1 | 0.1 | 0.1 |
| | | 295 | 0.1 | 2.6 | 96.4 | 0.8 | 5.4 | 84.2 | 6.2 | 0.3 | 0.3 | 0.1 |
| | | 315 | 0.1 | 3.6 | 95.2 | 1.1 | 10.0 | 72.3 | 11.0 | 0.6 | 0.9 | 0.3 |
| | | 335 | 0.1 | 4.2 | 94.4 | 1.4 | 10.1 | 67.8 | 14.3 | 0.8 | 1.0 | 0.4 |
| 3 | 35-DMA | 250 | 2.8 | 1.3 | 95.8 | 0.0 | 0.2 | 1.4 | 0.4 | 0.0 | 2.0 | 91.9 |
| | | 325 | 1.4 | 1.5 | 97.1 | 0.0 | 0.4 | 1.2 | 2.3 | 0.2 | 5.5 | 87.5 |
| | | 345 | 1.5 | 2.4 | 96.1 | 0.0 | 0.6 | 1.6 | 3.3 | 0.4 | 7.1 | 83.0 |
| | | 365 | 1.6 | 4.0 | 94.4 | 0.0 | 0.9 | 2.2 | 5.2 | 0.6 | 9.9 | 75.7 |
| 4 | 23-DMA | 270 | 1.2 | 0.6 | 98.2 | 0.0 | 96.6 | 0.3 | 1.0 | 0.0 | 0.0 | 0.0 |
| | (5 vol | 345 | 1.2 | 1.9 | 96.9 | 0.0 | 89.7 | 5.6 | 1.0 | 0.4 | 0.1 | 0.0 |
| | % in | 365 | 1.6 | 2.3 | 96.0 | 0.1 | 79.8 | 11.7 | 2.7 | 0.9 | 0.8 | 0.1 |
| | benz) | 405 | 1.5 | 9.0 | 88.0 | 1.5 | 17.9 | 28.5 | 24.4 | 5.7 | 6.2 | 5.3 |
| 5 | 34-DMA | 280 | 2.4 | 2.6 | 95.0 | 0.0 | 0.0 | 0.2 | 0.2 | 0.0 | 94.4 | 0.0 |
| | (20 | 320 | 1.7 | 5.2 | 93.0 | 0.0 | 0.3 | 0.6 | 0.7 | 0.0 | 89.8 | 1.6 |
| | vol % | 360 | 1.5 | 11.0 | 87.4 | 0.1 | 0.8 | 3.1 | 2.9 | 0.0 | 66.7 | 13.8 |
| | in | 380 | 1.3 | 14.5 | 83.7 | 0.4 | 3.7 | 6.5 | 7.3 | 1.6 | 41.7 | 22.9 |
| | benz) | 400 | 2.1 | 23.1 | 73.1 | 1.6 | 4.5 | 9.5 | 11.9 | 3.4 | 19.9 | 24.0 |
| | | 425 | 3.5 | 27.6 | 66.1 | 2.8 | 5.4 | 10.7 | 15.0 | 4.3 | 10.9 | 19.8 |
| 6 | 26-DMA | 265 | 0.0 | 0.6 | 97.6 | 1.8 | 0.0 | 0.7 | 1.0 | 95.8 | 0.0 | 0.0 |
| | (10 | 300 | 0.0 | 6.3 | 89.2 | 4.5 | 0.3 | 1.4 | 7.1 | 80.4 | 0.0 | 0.0 |
| | vol % | 330 | 0.3 | 8.7 | 87.3 | 3.7 | 3.6 | 8.5 | 23.8 | 48.8 | 0.8 | 1.8 |
| | in benz) | 370 | 1.7 | 18.2 | 78.0 | 2.2 | 8.8 | 16.3 | 25.9 | 11.8 | 6.5 | 8.7 |

Abbreviations used:
anil — aniline
benz — benzene
tol — toluidine

EXAMPLES 7-17

Isomerization of Dimethylanaline

Isomerization of DMA when contacted with acidic zeolite omega was further demonstrated by passing a liquid feed comprised of a DMA feed at a rate of 1.5 mL/h along with nitrogen carrier gas at a rate of 5 mL/min at atmospheric pressure over various forms of acidic zeolite omega in the reactor described in Example 1. Since the liquid feed was comprised of a DMA, there were 2 methyl groups per aniline ring in the feed and the number of methyl groups per aniline ring (Me/Ring) in the product should also be 2 if no methyl groups were lost.

EXAMPLE 7

The isomerization procedure described above was conducted employing a DMA feed comprised of 10%

EXAMPLE 8

The isomerization procedure described in Example 7 was substantially repeated except that a zeolite Ce-omega catalyst was employed. The catalyst was prepared as follows. The commercial zeolite omega described in Example 7 was refluxed at 100° for two hours with a solution made by placing about a 3-fold molar excess of cerium nitrate in water to effect a cation exchange. The resulting solution was then filtered and the zeolite so obtained was calcined at about 550° for about 16 hours. The zeolite was then refluxed for two hours in the cerium nitrate solution described above, filtered, and calcined at about 550° for about 16 hours to yield the catalyst. The reaction temperature, product composition and Me/Ring are shown in Table II.

EXAMPLE 9

The isomerization procedure described in Example 7 was substantially repeated except that a zeolite H-omega catalyst was employed. The catalyst was prepared as follows. The commercial zeolite omega described in Example 1 was refluxed at 100° for two hours with water. The zeolite was separated from the water by filtering and the zeolite so obtained was calcined at about 550° for about 16 hours. The zeolite was then refluxed for two hours in the water as above, filtered, and calcined at about 450° for about 16 hours to yield the catalyst. The reaction temperature, product composition and Me/Ring are shown in Table II.

EXAMPLE 10

The isomerization procedure described in Example 7 was substantially repeated except that the DMA feed was comprised of 10% by volume of 2,4-DMA in benzene and 0.8 g of the commercial zeolite H-omega described in Example 1 was employed as catalyst. The reaction temperature, product composition and Me/Ring are shown in Table II.

EXAMPLE 11

The isomerization procedure described in Example 10 was substantially repeated except that 1.0 g of zeolite H-omega catalyst was employed. The catalyst was prepared as follows. The commercial zeolite omega described in Example 7 was refluxed at 100° for two hours with water to effect a cation exchange. The resulting zeolite was separated from the water by filtering and the zeolite so obtained refluxed at 100° for one hour with water, filtered, refluxed at 100° for one hour with water, filtered and then calcined at about 450° for about 16 hours to yield the catalyst. The reaction temperature, product composition and Me/Ring are shown in Table II.

EXAMPLE 12

The isomerization procedure described in Example 10 was substantially repeated except that a 0.9 g of a zeolite Al-omega catalyst was employed. The catalyst was prepared as follows. The commercial zeolite omega described in Example 7 was refluxed at 100° for two hours with a solution made by placing about a 3-fold molar excess of aluminum nitrate in water to effect a cation exchange. The solution was then filtered and the zeolite so obtained was refluxed as above for one hour, filtered, refluxed as above for one hour, filtered and then calcined at about 450° for about 16 hours to yield the catalyst. The reaction temperature, product composition and Me/Ring are shown in Table II.

EXAMPLE 13

The isomerization procedure described in Example 10 was substantially repeated except that a 1.0 g of a zeolite Cu-omega catalyst was employed. The catalyst was prepared as follows. The commercial zeolite omega described in Example 7 was refluxed at 100° for one hour with a solution made by placing about a 3-fold molar excess of copper nitrate in water to effect a cation exchange. The solution was then filtered and the zeolite so obtained was refluxed as above for one hour, filtered, refluxed as above for one hour, filtered and then calcined at about 500° for about 16 hours to yield the catalyst. The reaction temperature, product composition and Me/Ring are shown in Table II.

EXAMPLES 14–17

The isomerization procedure described in Example 10 was substantially repeated four times except that 1.0 g amounts of zeolite Co-, Cr-, Sr-, and Fe-omega catalysts were employed. The catalysts were prepared as follows. In each example, the commercial zeolite omega described in Example 7 was refluxed at 100° for two hours with a solution made by placing about a 3-fold molar excess of cobalt, chromium, strontium, and iron nitrate, respectively, in water to effect a cation exchange. The resulting solutions were then filtered and the zeolites so obtained were refluxed as above for two hours, filtered then calcined at about 500° for about 16 hours to yield the catalysts. The resulting zeolite Co-omega, Cr-omega, Sr-omega and Fe-omega catalysts were used in Examples 14, 15, 16, and 17, respectively. The reaction temperatures, product compositions and Me/Ring are shown in Table II.

TABLE II

| Ex. No. | React. Temp. (°) | Product Composition (mole %) | | | | Individual DMA's | | | | | | Me/Ring |
|---|---|---|---|---|---|---|---|---|---|---|---|---|
| | | Anil | Tols | DMA's | TMA & TETRA | 23 | 24 | 25 | 26 | 34 | 35 | |
| 7 | 450 | 0.2 | 0.6 | 97.9 | 1.3 | 0.9 | 1.5 | 95.0 | 0.4 | 0.1 | 0.0 | 2.00 |
|   | 500 | 0.2 | 6.3 | 87.4 | 6.0 | 0.5 | 2.5 | 82.3 | 1.0 | 0.6 | 0.5 | 1.99 |
|   | 550 | 0.4 | 16.3 | 73.7 | 9.5 | 1.4 | 3.6 | 63.3 | 1.8 | 1.8 | 1.8 | 1.92 |
| 8 | 400 | 0.0 | 11.6 | 73.9 | 14.4 | 0.8 | 3.1 | 67.0 | 0.7 | 1.7 | 0.7 | 2.00 |
|   | 450 | 0.5 | 21.3 | 65.1 | 13.1 | 2.4 | 3.7 | 52.1 | 1.5 | 3.2 | 2.1 | 1.91 |
|   | 500 | 0.3 | 15.8 | 72.8 | 11.0 | 1.8 | 2.9 | 64.3 | 1.0 | 1.8 | 1.2 | 1.95 |
| 9 | 400 | 0.1 | 6.5 | 88.5 | 4.8 | 0.5 | 3.4 | 82.2 | 1.0 | 0.6 | 0.8 | 1.98 |
|   | 450 | 0.0 | 8.9 | 82.6 | 8.4 | 1.0 | 4.0 | 72.4 | 1.8 | 1.2 | 2.2 | 2.00 |
|   | 500 | 0.5 | 17.0 | 71.7 | 10.8 | 2.0 | 5.4 | 55.7 | 2.6 | 2.0 | 3.9 | 1.93 |
| 10 | 400 | 0.6 | 10.7 | 84.0 | 4.7 | 1.6 | 74.5 | 5.2 | 1.1 | 0.9 | 0.7 | 1.93 |
|   | 450 | 1.0 | 14.8 | 76.2 | 8.0 | 2.2 | 64.3 | 6.0 | 1.5 | 1.5 | 0.7 | 1.91 |
|   | 500 | 1.7 | 16.9 | 73.7 | 7.7 | 2.1 | 61.6 | 5.7 | 1.4 | 1.9 | 0.9 | 1.88 |
| 11 | 400 | 1.7 | 10.6 | 77.9 | 1.0 | 11.7 | 45.5 | 16.0 | 2.0 | 1.5 | 1.2 | 1.96 |
|   | 450 | 1.7 | 17.4 | 70.9 | 1.0 | 8.3 | 39.6 | 16.1 | 2.9 | 2.3 | 1.8 | 1.89 |
|   | 500 | 0.6 | 13.8 | 76.9 | 0.9 | 6.3 | 56.5 | 10.3 | 1.6 | 1.4 | 0.8 | 1.94 |
| 12 | 400 | 11.3 | 14.7 | 58.3 | 25.8 | 8.4 | 15.2 | 20.2 | 7.0 | 3.0 | 4.5 | 2.09 |
|   | 425 | 3.0 | 19.0 | 53.1 | 25.0 | 7.8 | 12.0 | 17.7 | 6.0 | 3.8 | 5.8 | 2.00 |
|   | 450 | 8.2 | 33.4 | 46.4 | 11.7 | 6.4 | 14.4 | 14.8 | 5.7 | 1.8 | 3.5 | 1.62 |
|   | 500 | 0.2 | 7.7 | 85.9 | 6.1 | 0.3 | 82.7 | 1.8 | 1.1 | 0.0 | 0.0 | 1.98 |
| 13 | 400 | 0.2 | 4.5 | 92.6 | 2.7 | 0.3 | 89.9 | 1.7 | 0.7 | 0.2 | 0.0 | 1.98 |
|   | 450 | 1.0 | 13.1 | 78.8 | 7.2 | 0.8 | 73.2 | 2.6 | 1.6 | 0.5 | 0.1 | 1.92 |
|   | 500 | 1.4 | 16.7 | 71.4 | 10.5 | 1.2 | 63.1 | 3.9 | 2.0 | 1.0 | 0.3 | 1.91 |
| 14 | 250 | 0.5 | 1.0 | 98.2 | 0.4 | 0.0 | 96.3 | 1.2 | 0.6 | 0.0 | 0.0 | 1.99 |
|   | 350 | 0.0 | 3.0 | 95.3 | 1.6 | 1.6 | 90.3 | 2.7 | 0.6 | 0.1 | 0.0 | 1.99 |
|   | 400 | 0.2 | 5.5 | 90.7 | 3.6 | 5.2 | 76.1 | 7.4 | 1.0 | 0.7 | 0.2 | 1.98 |

TABLE II-continued

| Ex. No. | React. Temp. (°) | Product Composition (mole %) | | | | Individual DMA's | | | | | | Me/ Ring |
|---|---|---|---|---|---|---|---|---|---|---|---|---|
| | | Anil | Tols | DMA's | TMA & TETRA | 23 | 24 | 25 | 26 | 34 | 35 | |
| | 450 | 2.1 | 21.6 | 60.6 | 15.7 | 1.6 | 49.9 | 3.9 | 3.7 | 1.3 | 0.3 | 1.90 |
| 15 | 250 | 0.0 | 1.4 | 98.0 | 0.5 | 0.0 | 96.4 | 1.1 | 0.5 | 0.0 | 0.0 | 1.99 |
| | 400 | 0.9 | 3.4 | 93.0 | 3.2 | 0.0 | 91.0 | 1.2 | 0.6 | 0.1 | 0.0 | 1.98 |
| | 450 | 0.3 | 8.6 | 83.9 | 7.2 | 0.3 | 80.4 | 1.8 | 0.9 | 0.4 | 0.0 | 1.98 |
| | 500 | 1.1 | 12.4 | 78.3 | 8.2 | 0.4 | 74.1 | 2.0 | 1.1 | 0.5 | 0.2 | 1.94 |
| 16 | 250 | 0.9 | 1.7 | 97.0 | 0.4 | 0.0 | 95.4 | 1.0 | 0.5 | 0.0 | 0.2 | 1.97 |
| | 350 | 0.0 | 3.2 | 95.1 | 1.6 | 0.6 | 92.2 | 1.7 | 0.5 | 0.0 | 0.0 | 1.98 |
| | 400 | 0.1 | 4.1 | 92.7 | 3.1 | 2.0 | 86.2 | 3.5 | 0.6 | 0.3 | 0.0 | 1.99 |
| | 450 | 0.3 | 6.9 | 87.8 | 4.9 | 4.5 | 73.9 | 7.2 | 1.0 | 0.9 | 0.2 | 1.97 |
| | 500 | 1.1 | 14.1 | 74.3 | 10.5 | 4.5 | 57.8 | 7.8 | 1.8 | 2.0 | 0.6 | 1.94 |
| 17 | 300 | 0.0 | 2.8 | 96.2 | 0.9 | 0.0 | 94.6 | 1.1 | 0.6 | 0.0 | 0.0 | 1.98 |
| | 400 | 0.3 | 7.0 | 88.5 | 4.1 | 0.0 | 86.6 | 1.0 | 0.7 | 0.0 | 0.1 | 1.96 |
| | 500 | 2.0 | 10.3 | 81.2 | 6.4 | 0.2 | 78.4 | 1.2 | 1.1 | 0.2 | 0.2 | 1.92 |

EXAMPLES 18-21

Isomerization of 2,4-DMA

Isomerization of 2,4-DMA when contacted with acidic zeolites beta, H-beta, L and H-L was demonstrated by passing a liquid feed comprised of 2,4-DMA (10 volume in benzene) at a rate of 1.5 mL/h along with nitrogen carrier gas at the rate of 5 mL/min at atmospheric pressure over 1 g of acidic zeolite in the reactor described in Examples 1-6. The products were analyzed using gas chromatography as described for Example 1.

EXAMPLE 18

The isomerization procedure described above was conducted employing zeolite H-beta as catalyst. The catalyst was prepared as follows. A mixture composed of 11.6 g of Na aluminate, 290.7 g of a colloidal silica commercially available from E. I. duPont de Nemours and Company under the registered trademark Ludox ® HS-40, and 116 mL of a 25% solution of tetraethylammonium hydroxide was heated in a Hastelloy C autoclave under autogeneous conditions at 150° for 6 days. The resulting product was washed and heated to 500° for 1 hour to remove the organic template. X-ray diffration indicated that the product was zeolite Na-beta as indicated in U.S. Pat. No. 3,308,069, the disclosure of which is incorporated herein by reference. This material was then contacted three times with a 10% NH$_4$NO$_3$ solution at 80°. The resulting zeolite NH$_4$-beta was converted to zeolite H-beta by calcination at 700° for 4 hours under deep bed conditions. The reaction temperatures and the product compositions are shown in Table III.

EXAMPLE 19

The isomerization procedure described in Example 18 was substantially repeated except that zeolite Al-beta was employed as catalyst. The catalyst was prepared as follows. 2 g of the zeolite H-beta made as described in Example 18 was refluxed at 100° for two hours with 25 mL of a solution, made by placing 28 g of aluminum nitrate in 100 mL of distilled water, to effect a cation exchange. The solution was then filtered. The zeolite was then refluxed for two hours in the aluminum nitrate solution as above, filtered, and calcined at about 100° for about ½ hour, at about 250° for about ½ hour and then at about 550° for about 16 hours to yield the catalyst. The reaction temperatures and the product compositions are shown in Table III.

EXAMPLE 20

The isomerization procedure described in Example 18 was substantially repeated except that zeolite H-L was employed as catalyst. The catalyst was prepared as follows. A zeolite commercially available from Union Carbide as ELZ-L was contacted two times for 12 hours each time with a 10% NH$_4$NO$_3$ solution at 90°. The resulting zeolite was calcined at 500° for 10 hours and blended with 5% of the polyethylene oxide described in Example 1 which served as a binder for the zeolite. The resulting combination was molded into a 1 inch (2.54 cm) diameter pellet which was then crushed and seived to yield a −20/+40 mesh powder (ASTM Standard Sieve Units 425 μm/850 μm). The powder was heated to 350° to remove the binder and yield the catalyst. The reaction temperatures and the product compositions are shown in Table III.

EXAMPLE 21

The procedure described in Example 18 was substantially repeated except that zeolite Al-L was employed as catalyst. The catalyst was prepared as follows. 2 g of the zeolite H-L described in Example 20 were refluxed at 100° for two hours with 25 mL of a solution, made by placing 28 g of aluminum nitrate in 100 mL of distilled water, to effect a cation exchange. The solution was then filtered. The zeolite was then refluxed for two hours in the aluminum nitrate solution as above, filtered, and calcined at about 100° for about ½ hour, at about 250° for about ½ hour and then at about 550° for about 16 hours to yield the catalyst. The reaction temperatures and the product compositions are shown in Table III.

EXAMPLE 22

Isomerization of 2,5-DMA when contacted with acidic zeolite H-L was demonstrated by passing a liquid feed comprised of 2,5-DMA at a rate of 3 mL/h along with nitrogen carrier gas at the rate of 10 mL/min at atmospheric pressure over 3 g of acidic zeolite catalyst in the reactor described in Example 1. The catalyst was the zeolite H-L described in Example 20. The product was analyzed using gas chromatography as described for Example 1. The reaction temperatures and the product compositions are shown in Table III.

EXAMPLE 23

Isomerization of 2,5-DMA when contacted with acidic zeolite H-beta was demonstrated by passing a liquid feed comprised of 2,5-DMA and m-toluidine (1:1 molar) at a rate of 3 mL/h along with nitrogen carrier gas at the rate of 10 mL/min at atmospheric pressure over 3 g of acidic zeolite catalyst in the reactor described in Example 1. The H-beta catalyst was prepared by the method described in Example 18. An X-ray diffration pattern of the product showed it to be primarily zeolite beta with a trace of $SiO_2$ impurity The Na,tetraethylammonium-beta zeolite was contacted three times with a 10% $NH_4NO_3$ solution to produce $NH_4$, tetraethylammonium-beta zeolite which was heated to 540°. The exchange and calcination procedure was repeated once more time to produce zeolite H-beta. This zeolite H-beta was blended with 10% of the polyethylene oxide described in Example 1. The resulting combination was molded into a 1 inch (2.54 cm) diameter pellet which was then crushed and seived to yield a −20/+40 mesh powder (ASTM Standard Sieve Units—425 μm/850 μm). The powder was heated to 350° to remove the binder and yield the catalyst. The product was analyzed using gas chromatography as described for Example 1. The reaction temperatures and the product compositions are shown in Table III.

atmospheric pressure over 3 g zeolite H-omega catalyst in the reactor described in Example 1. The catalyst was the commercial zeolite H-omega catalyst described in Example 1. The reaction products were analyzed using gas chromatography as described for Example 1.

EXAMPLE 24

The isomerization procedure described above was conducted employing a TMA feed comprised of 10% by volume of 2,4,6-TMA in benzene and the nitrogen carrier gas was fed at a rate of 5 mL/min. The reaction temperatures and product compositions are shown in Table IV.

EXAMPLE 25

The isomerization procedure described in Example 24 was substantially repeated except that the TMA feed comprised of 10% by volume of 2,4,5-TMA in benzene and the nitrogen carrier gas was fed at a rate of 10 mL/min. The reaction temperatures and product compositions are shown in Table IV.

TABLE III

| Ex. No. | React. Temp. (°) | Product Composition (mole %) | | | | Individual DMA's | | | | |
|---|---|---|---|---|---|---|---|---|---|---|
| | | Anil | Tols | DMA's | TMA & TETRA | 23 | 24 | 25 | 26 | 34 | 35 |
| 18 | 250 | 0.0 | 3.7 | 95.0 | 1.1 | 0.0 | 93.7 | 0.7 | 0.6 | 0.0 | 0.0 |
| | 300 | 0.3 | 14.6 | 75.8 | 7.5 | 1.8 | 70.9 | 3.4 | 1.2 | 0.3 | 0.0 |
| | 350 | 1.5 | 23.2 | 61.4 | 13.9 | 5.8 | 33.6 | 14.3 | 2.8 | 2.3 | 2.6 |
| | 400 | 2.8 | 26.4 | 56.2 | 14.6 | 5.4 | 14.7 | 15.6 | 7.8 | 5.0 | 7.7 |
| | 450 | 7.9 | 35.4 | 42.6 | 11.6 | 4.8 | 11.8 | 13.1 | 3.6 | 5.0 | 6.9 |
| | 500 | 24.8 | 45.0 | 25.3 | 4.9 | 2.8 | 4.9 | 6.8 | 2.2 | 3.3 | 5.3 |
| 19 | 250 | 0.0 | 4.4 | 94.9 | 0.7 | 0.0 | 93.6 | 0.8 | 0.5 | 0.0 | 0.0 |
| | 300 | 0.0 | 10.1 | 85.7 | 4.3 | 0.0 | 84.1 | 0.8 | 0.8 | 0.0 | 0.0 |
| | 350 | 0.6 | 17.8 | 69.2 | 11.9 | 0.5 | 64.9 | 1.4 | 2.7 | 0.2 | 0.0 |
| | 400 | 1.4 | 20.7 | 66.1 | 11.8 | 3.2 | 50.7 | 8.2 | 2.1 | 1.4 | 0.5 |
| | 450 | 1.8 | 23.1 | 45.1 | 13.2 | 5.7 | 13.9 | 16.0 | 4.2 | 5.3 | 8.1 |
| 20 | 250 | 0.0 | 0.4 | 99.4 | 0.1 | 0.0 | 97.7 | 1.1 | 0.6 | 0.0 | 0.0 |
| | 300 | 0.0 | 1.9 | 96.6 | 1.4 | 0.0 | 95.0 | 1.0 | 0.6 | 0.0 | 0.0 |
| | 350 | 0.1 | 4.1 | 92.6 | 2.9 | 0.3 | 90.2 | 1.3 | 0.7 | 0.1 | 0.0 |
| | 400 | 0.3 | 9.1 | 84.1 | 6.7 | 1.1 | 78.3 | 2.8 | 1.2 | 0.5 | 0.2 |
| | 450 | 0.7 | 12.1 | 78.0 | 9.0 | 3.6 | 62.9 | 7.7 | 1.6 | 1.5 | 0.7 |
| | 500 | 1.0 | 15.8 | 65.2 | 18.0 | 4.6 | 43.2 | 10.9 | 1.9 | 2.9 | 1.7 |
| 21 | 250 | 0.0 | 0.9 | 98.6 | 0.2 | 0.0 | 97.0 | 1.1 | 0.5 | 0.0 | 0.0 |
| | 300 | 0.0 | 3.8 | 93.9 | 2.0 | 0.1 | 91.9 | 1.0 | 0.9 | 0.0 | 0.0 |
| | 350 | 0.3 | 4.9 | 92.1 | 2.5 | 0.4 | 88.6 | 1.8 | 0.9 | 0.3 | 0.1 |
| | 400 | 1.3 | 8.6 | 85.0 | 5.1 | 1.5 | 76.4 | 4.3 | 1.2 | 1.0 | 0.6 |
| | 450 | 1.1 | 12.1 | 79.4 | 7.5 | 3.2 | 63.8 | 7.8 | 1.4 | 2.1 | 1.1 |
| | 500 | 1.8 | 17.9 | 69.0 | 11.4 | 4.6 | 45.6 | 11.1 | 2.2 | 3.4 | 2.1 |
| 22 | 370 | 0.2 | 7.2 | 84.8 | 6.7 | 0.8 | 3.7 | 77.4 | 1.4 | 0.7 | 0.8 |
| | 390 | 0.3 | 10.4 | 79.1 | 8.6 | 1.0 | 4.8 | 69.0 | 1.9 | 1.2 | 1.2 |
| | 410 | 0.3 | 10.7 | 79.4 | 8.2 | 1.1 | 4.7 | 69.1 | 1.9 | 1.2 | 1.4 |
| 23 | 310 | 1.5 | 52.7 | 39.8 | 5.3 | 1.6 | 0.7 | 31.9 | 0.8 | 4.0 | 0.8 |
| | 330 | 2.2 | 56.4 | 36.6 | 3.9 | 1.7 | 1.7 | 27.4 | 1.3 | 3.4 | 1.1 |
| | 370 | 5.1 | 56.5 | 33.6 | 3.6 | 2.1 | 1.9 | 24.0 | 1.2 | 3.2 | 1.2 |
| | 390 | 4.5 | 57.2 | 33.9 | 3.1 | 2.1 | 2.5 | 23.6 | 1.2 | 3.1 | 1.4 |
| | 410 | 3.7 | 57.7 | 34.3 | 3.2 | 1.9 | 2.5 | 24.7 | 1.1 | 3.0 | 1.1 |

EXAMPLES 24–26

Isomerization of Trimethylaniline

Isomerization of trimethylaniline (TMA) when contacted with zeolite omega was demonstrated by passing a liquid feed, comprised of a TMA feed in benzene at a rate of 3.0 mL/h along with nitrogen carrier gas at

EXAMPLE 26

The isomerization procedure described in Example 24 was substantially repeated except that the nitrogen carrier gas was fed at a rate of 10 mL/min. The reaction temperatures and product compositions are shown in Table IV.

TABLE IV

| Ex. No. | React. Temp. (°) | Product Composition (mole %) | | | | | Individual TMA's | | | | | |
|---|---|---|---|---|---|---|---|---|---|---|---|---|
| | | Tols | DMA's | TMA's | Tetra | Penta | 246 | 245 | 236 | 235 | 345 | 234 |
| 24 | 280 | 0.0 | 4.2 | 90.2 | 5.0 | 0.0 | 87.0 | 0.2 | 3.0 | 0.0 | 0.0 | 0.0 |
| | 300 | 0.0 | 4.6 | 89.4 | 6.4 | 0.0 | 81.0 | 1.0 | 7.0 | 0.4 | 0.0 | 0.0 |
| | 320 | 0.0 | 2.9 | 78.5 | 19.0 | 0.0 | 56.0 | 7.0 | 13.0 | 2.0 | 0.4 | 0.0 |

TABLE IV-continued

| Ex. No. | React. Temp. (°) | Product Composition (mole %) | | | | | Individual TMA's | | | | | |
|---|---|---|---|---|---|---|---|---|---|---|---|---|
| | | Tols | DMA's | TMA's | Tetra | Penta | 246 | 245 | 236 | 235 | 345 | 234 |
| | 340 | 0.0 | 4.2 | 75.4 | 20.0 | 1.0 | 43.0 | 8.0 | 16.0 | 7.0 | 1.0 | 0.4 |
| | 360 | 0.0 | 5.3 | 67.0 | 17.0 | 2.0 | 25.0 | 12.0 | 15.0 | 12.0 | 2.0 | 1.0 |
| | 380 | 0.0 | 8.4 | 63.0 | 28.0 | 1.0 | 14.0 | 14.0 | 13.0 | 15.0 | 4.0 | 3.0 |
| | 400 | 0.0 | 10.0 | 60.0 | 28.0 | 2.0 | 10.0 | 16.0 | 11.0 | 17.0 | 3.0 | 3.0 |
| | 420 | 0.0 | 17.0 | 54.2 | 28.0 | 2.0 | 8.0 | 16.0 | 9.0 | 17.0 | 4.0 | 0.2 |
| 25 | 300 | 0.0 | 2.4 | 95.7 | 1.9 | 0.0 | 0.3 | 90.6 | 0.6 | 2.6 | 1.3 | 0.3 |
| | 320 | 0.0 | 4.0 | 93.3 | 2.6 | 0.0 | 1.0 | 79.7 | 1.7 | 7.6 | 2.6 | 0.8 |
| | 340 | 0.0 | 4.0 | 93.3 | 2.6 | 0.0 | 2.5 | 63.1 | 3.9 | 14.9 | 3.9 | 2.1 |
| | 360 | 0.2 | 7.9 | 86.1 | 5.8 | 0.0 | 5.1 | 48.2 | 6.4 | 19.8 | 4.2 | 2.6 |
| | 420 | 1.2 | 20.9 | 62.8 | 15.0 | 0.0 | 10.4 | 20.3 | 8.7 | 17.5 | 3.2 | 2.7 |
| 26 | 250 | 0.0 | 2.3 | 96.3 | 1.2 | 0.0 | 94.4 | 0.2 | 1.7 | 0.0 | 0.0 | 0.0 |
| | 350 | 0.0 | 3.3 | 76.5 | 2.9 | 0.0 | 61.8 | 2.5 | 11.0 | 1.3 | 0.0 | 0.0 |
| | 400 | 0.0 | 7.0 | 86.0 | 7.0 | 0.0 | 43.0 | 12.3 | 18.2 | 10.9 | 1.6 | 0.0 |
| | 450 | 0.0 | 19.3 | 68.1 | 12.7 | 0.0 | 18.7 | 16.5 | 12.4 | 16.0 | 2.9 | 1.6 |

Abbreviations used:
tol — toluidine
tetra — tetramethylanilines
penta — pentamethylaniline

What is claimed is:

1. A process for preparing an isomeric mixture of methyl-substituted anilines having the formula:

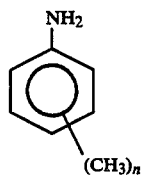

(I)

wherein n is 2 or 3, said process comprising
(A) contacting at least one compound of the formula

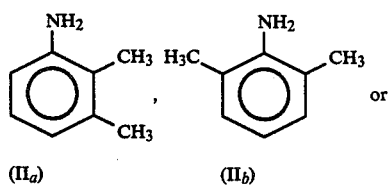

(II$_a$)  (II$_b$)

or

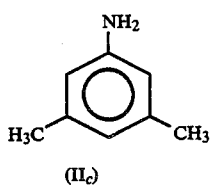

(II$_c$)

with an acidic zeolite catalyst at a temperature of from about 240° C. to about 550° C. and at a pressure of from about 10 kPa to about 10 MPa, said zeolite catalyst being selected from the group consisting of zeolites omega, beta, L and mixtures thereof, or
(B) contacting at least one compound of the formula

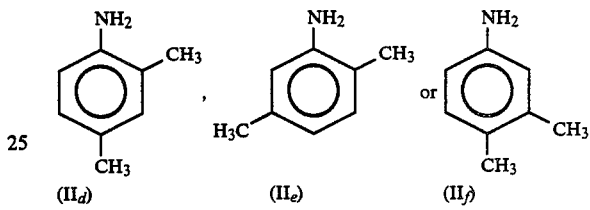

(II$_d$)  (II$_e$)  (II$_f$)

with an acidic zeolite catalyst at a temperature of from about 240° C. to about 550° C. and at a pressure of from about 10 kPa to about 10 MPa, said zeolite catalyst being selected from the group consisting of zeolites omega, beta, L and mixtures thereof, and isolating from said isomeric mixture a portion of said mixture which comprises at least one compound of formula IIa, IIb or IIc.

2. A process according to claim 1, wherein the acidic zeolite catalyst is zeolite omega.

3. A process according to claim 2, wherein the acidic zeolite omega is the hydrogen or aluminum form.

4. A process according to claim 3, wherein the temperature is from about 280° C. to about 425° C.

5. A process according to claim 4, wherein the pressure is from about 100 kPa to about 1 MPa.

6. A process according to claim 5, wherein the reaction time is from about 0.1 second to about 10 hours.

7. A process according to claim 1, wherein the acidic zeolite catalyst is zeolite beta.

8. A process according to claim 7, wherein the acidic zeolite beta is the hydrogen or aluminum form.

9. A process according to claim 8, wherein the temperature is from about 280° C. to about 425° C.

10. A process according to claim 9, wherein the pressure is from about 100 kPa to about 1 MPa.

11. A process according to claim 10, wherein the reaction time is from about 0.1 second to about 10 hours.

12. A process according to claim 1, wherein the acidic zeolite catalyst is zeolite L.

13. A process according to claim 12, wherein the acidic zeolite L is the hydrogen or aluminum form.

14. A process according to claim 13, wherein the temperature is from about 280° C. to about 425° C.

15. A process according to claim 14, wherein the pressure is from about 100 kPa to about 1 MPa.

16. A process according to claim 15, wherein the reaction time is from about 0.1 second to about 10 hours.

* * * * *